United States Patent [19]
Yoshii et al.

[11] Patent Number: 5,652,657
[45] Date of Patent: Jul. 29, 1997

[54] INSPECTION SYSTEM FOR ORIGINAL WITH PELLICLE

[75] Inventors: Minoru Yoshii, Tokyo; Michio Kohno, Utsunomiya; Seiya Miura, Utsunomiya; Kyoichi Miyazaki, Utsunomiya; Toshihiko Tsuji, Utsunomiya; Seiji Takeuchi, Utsunomiya, all of Japan

[73] Assignee: Canon Kabushiki Kaisha, Tokyo, Japan

[21] Appl. No.: 467,922

[22] Filed: Jun. 6, 1995

[30] Foreign Application Priority Data

Jun. 6, 1994 [JP] Japan .................................. 6-147137

[51] Int. Cl.⁶ .................................................. G01B 11/00
[52] U.S. Cl. ...................... 356/394; 356/237; 356/239
[58] Field of Search ................................ 356/394, 237, 356/239, 372, 362

[56] References Cited

U.S. PATENT DOCUMENTS

| | | | |
|---|---|---|---|
| 3,734,626 | 5/1973 | Roberts et al. | 356/120 |
| 4,795,911 | 1/1989 | Kohno et al. | 250/572 |
| 4,831,274 | 5/1989 | Kohno et al. | 250/563 |
| 4,866,287 | 9/1989 | Weber | 250/571 |
| 4,886,975 | 12/1989 | Murakami et al. | 250/572 |
| 4,999,511 | 3/1991 | Kohno | 250/572 |
| 5,017,798 | 5/1991 | Murakami et al. | 250/572 |
| 5,098,191 | 3/1992 | Noguchi et al. | 356/394 |
| 5,106,194 | 4/1992 | Kuchel | 356/360 |
| 5,148,037 | 9/1992 | Suda et al. | 250/548 |
| 5,168,322 | 12/1992 | Clarke et al. | 356/394 |
| 5,200,800 | 4/1993 | Suda et al. | 356/401 |
| 5,270,794 | 12/1993 | Tsuji et al. | 356/371 |
| 5,291,023 | 3/1994 | Hasegawa et al. | 250/548 |
| 5,333,050 | 7/1994 | Nose et al. | 356/356 |
| 5,344,236 | 9/1994 | Fishman | 356/432 |

Primary Examiner—Frank Gonzalez
Assistant Examiner—Reginald A. Ratliff
Attorney, Agent, or Firm—Fitzpatrick, Cella, Harper & Scinto

[57] ABSTRACT

An inspection system inspecting an original with a pellicle, which system includes a light source for providing a light beam, a first detecting device for receiving light produced as a result of passage of the light beam through the pellicle, a second detecting device for receiving light produced as a result of non-passage of the light beam through the pellicle, and a processing system for determining information related to transmissivity of the pellicle, on the basis of outputs of the first and second detecting devices.

6 Claims, 11 Drawing Sheets

INSPECTION SYSTEM FOR ORIGINAL WITH PELLICLE

FIELD OF THE INVENTION AND RELATED ART

This invention relates to an inspection system for an original for use in the manufacture of semiconductor devices, for example. More particularly, the invention is concerned with an inspection system suitably usable to detect, with good precision, a non-transparent particle such as dust, if any, adhered to a surface (surface to be inspected) such as a surface of an original (such as a reticle or photomask) having a circuit pattern formed thereon and having a pellicle protection film mounted thereon.

Generally, in integrated (IC) manufacturing processes, a circuit pattern for photoprinting as formed on an original such as a reticle or photomask, is transferred onto a wafer having a resist coating by use of a semiconductor printing apparatus such as a stepper or mask aligner.

If, in this process, a particle such as dust or a pattern fault is present on the pattern surface, such a particle or fault is transferred to the wafer together with the circuit pattern. This directly decreases the yield of IC manufacture.

Particularly, if a circuit pattern is printed on a wafer repeatedly in accordance with the step-and-repeat method, the presence of a single particle on the reticle surface results in a large decrease of yield of IC manufacture since the particle is printed in every zone on the wafer surface. Thus, inspection of the presence of a particle on a substrate is required in the IC manufacturing process. While a variety of inspection methods have been proposed, in many cases, a method based on the isotropic light scattering property of a particle is used.

FIG. 12 shows the structure of a main portion of a known type particle inspecting system, which is arranged to detect the presence/absence of a particle by detecting scattered light from the particle.

In the drawing, a laser beam from a laser light source 151 is transformed into a laser beam best suited to the particle inspection, by means of a polarizer 152, a filter 153, a collimator system 154, for example, and then it is directed by a mirror 155 to a scanning optical system which comprises a scanning mirror 157 such as a polygonal mirror and an f-θ lens 158. A scanning laser beam from the f-θ lens 158 is collected as a scanning light spot 159 upon the surface 160 to be inspected (such as a surface of a reticle having a pattern formed thereon). By relatively moving the surface 160 by means of a scanning stage system 166 in a direction perpendicular to the scanning direction as defined by the scanning spot 159, the whole surface 160 is inspected.

A detection system which comprises a lens system 161, an aperture 163 and a photoelectric detector 164, is disposed at the back or side with respect to the incidence direction of the laser beam. The disposition of this detection system is so set that, since scattered light produced by the circuit pattern in response to projection of the laser beam upon the surface 160 has particular diffraction directions, the detection system is out of the diffraction directions and does not detect such scattered light.

In this structure, if no particle is present within the range of the scanning spot 159, no scattered light is detected by the photoelectric detector 164. If a particle is present, scattered light from a small particle advances isotropically and, thus, the photoelectric detector 164 detects scattered light. A detection signal obtainable therefrom is processed by a signal processing system 165, by which the presence/absence of a particle is performed.

Generally, the size of a particle and the quantity of scattered light are in an approximately proportional relation. Thus, the size of the particle is predictable from the quantity of the scattered light. In the procedure of original (substrate) inspection, first an inspection method such as described above is used to discriminate the absence of a particle of a damaging size upon the original and, then, a protection film (called a pellicle) is attached to the original so as to prevent further possible adhesion of particles on the original.

A pellicle film comprises a transparent film of macromolecules. The pellicle is supported by a spacer, called a pellicle supporting frame, at a distance of a few millimeters from the reticle surface (patterned surface) to thereby protect the circuit pattern on the reticle.

Generally, once a pellicle is attached to an original, there is no possibility of adhesion of a particle on a circuit pattern of the protected original. On the other hand, there is a possibility of adhesion of a particle or particles on the surface of the pellicle during the processes from the pellicle attachment to the exposure process.

However, if a particle is adhered to the surface of the pellicle, since the focal point position is just upon the circuit pattern surface of the reticle during the projection exposure process and thus the particle on the pellicle is out of an optically conjugate relation with a wafer and is defocused thereon, there is not a large possibility that the particle is transferred to the wafer to produce IC fault.

It is, however, possible that a particle is adhered to the circuit pattern surface of an original during a period from the inspection of the original before being protected by a pellicle to completion of pellicle attachment. It is, therefore, desirable to perform the inspection again to an original having a pellicle mounted thereon. Namely, it is desirable to inspect the reticle surface through a pellicle attached thereto.

Light passing a pellicle may cause multiple interference at the top and bottom surfaces of the pellicle film. The transmissivity and reflectivity of a pellicle have a relation to the thickness and refractivity of the thin film. Since in a particle inspecting system a light beam is projected obliquely to an original so as to obtain a higher signal-to-noise ratio (S/N ratio), a change in film thickness causes a large change in the quantity of light transmission and, therefore, a change in the quantity of light which reaches the surface of the original to be inspected.

As a result of this, the quantity of scattered light produced by a particle changes. This means that a change in the film thickness of a pellicle makes it difficult to predict the size of a particle. In consideration of such a problem, a proposal has been made in relation to a device for measuring the transmissivity of a pellicle.

FIG. 13 is a schematic view for explaining a known example of measuring the transmissivity of a pellicle. Denoted in the drawing at 4 is an original having a circuit pattern, and denoted at 5 is a pellicle supporting frame. Denoted at 6 is a pellicle film, and denoted at 910 is a light source such as a He—Ne laser, for example. Denoted at 911 is a half mirror, and denoted at 915 is a reflector having been made through chromium deposition, for example, being effective to reflect light. Denoted at 916a and 916b are photoelectric converters, respectively, for intensity monitoring an input laser and for intensity measuring to reflected light, respectively. The light 910 passes through the half mirror 911 and then through the pellicle 6, and it is reflected by the reflector 915. The light reflected thereby is reflected again by the half mirror 911, and it is received by the photoelectric converter 916b such that it is photoelectrically transformed.

Here, the intensity IR of the reflected light is given by:

$$Ii \times Ti^{**}2 \times MR \times 0.25 = IR$$

wherein Ii is the intensity of input light, Ti is the transmissivity of the pellicle, MR is the reflectivity of the reflector 915, and IR is the intensity of the reflected light, and wherein the ratio of transmissivity to reflectivity of the half mirror is taken as 50%.

The transmissivity Ti of the pellicle 6 is calculated in accordance with the following equation:

$$Ti = \sqrt{\{IR/(0.25 \times MR \times Ii)\}}$$

The arrangement described above, however, involves some inconveniences such as follows:

(1) In a case where the transmissivity of a pellicle is to be measured by using a reflector, only a measured value at the time of perpendicular light incidence is obtainable in the transmissivity measurement. Thus, it should be converted in terms of an incidence angle at the time of particle inspection (usually, 20 deg. to 40 deg.

(2) There is a necessity of conversion in terms of the wavelength to be used for the particle inspection. In many cases, an Ar laser (wavelength: 488 nm) is used for the inspection. If a He—Ne laser (wavelength: 633 nm) is used for measurement of the pellicle transmissivity, wavelength conversion is necessary.

(3) The reflectivity of the reflector has to be measured separately before the pellicle is attached. This requires additional operation.

SUMMARY OF THE INVENTION

It is an object of the present invention to provide a solution for at least one of the problems described above.

It is another object of the present invention to provide an inspection system by which inspection of an original is performed with higher precision and in a simple manner.

It is a further object of the present invention to provide an inspection system by which information related to the transmissivity of a pellicle attached to an original can be detected more accurately.

It is still a further object of the present invention to provide an inspection system in which information related to the transmissivity of a pellicle is detected by using a light source, provided for the inspection of an original, by which the inspection is facilitated and by which the structure of the inspection system is made simple.

It is yet a further object of the present invention to provide an exposure system and/or an inspection and cleaning system which uses one of the inspection systems described just above.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

[Embodiment 1]

Figure 1:
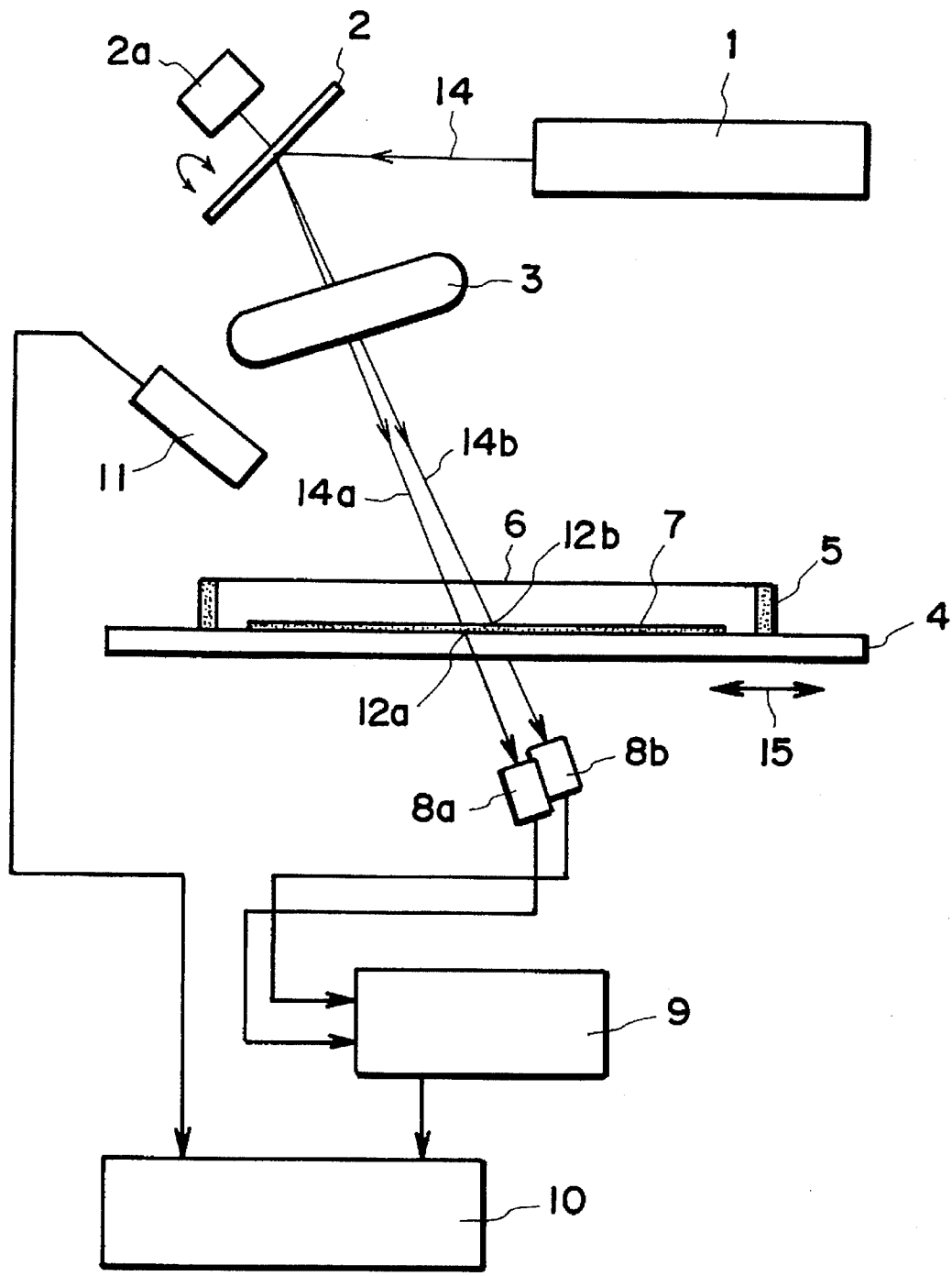
FIG. 1 is a schematic sectional view of a main portion of a particle inspection system according to a first embodiment of the present invention.
Figure 2:
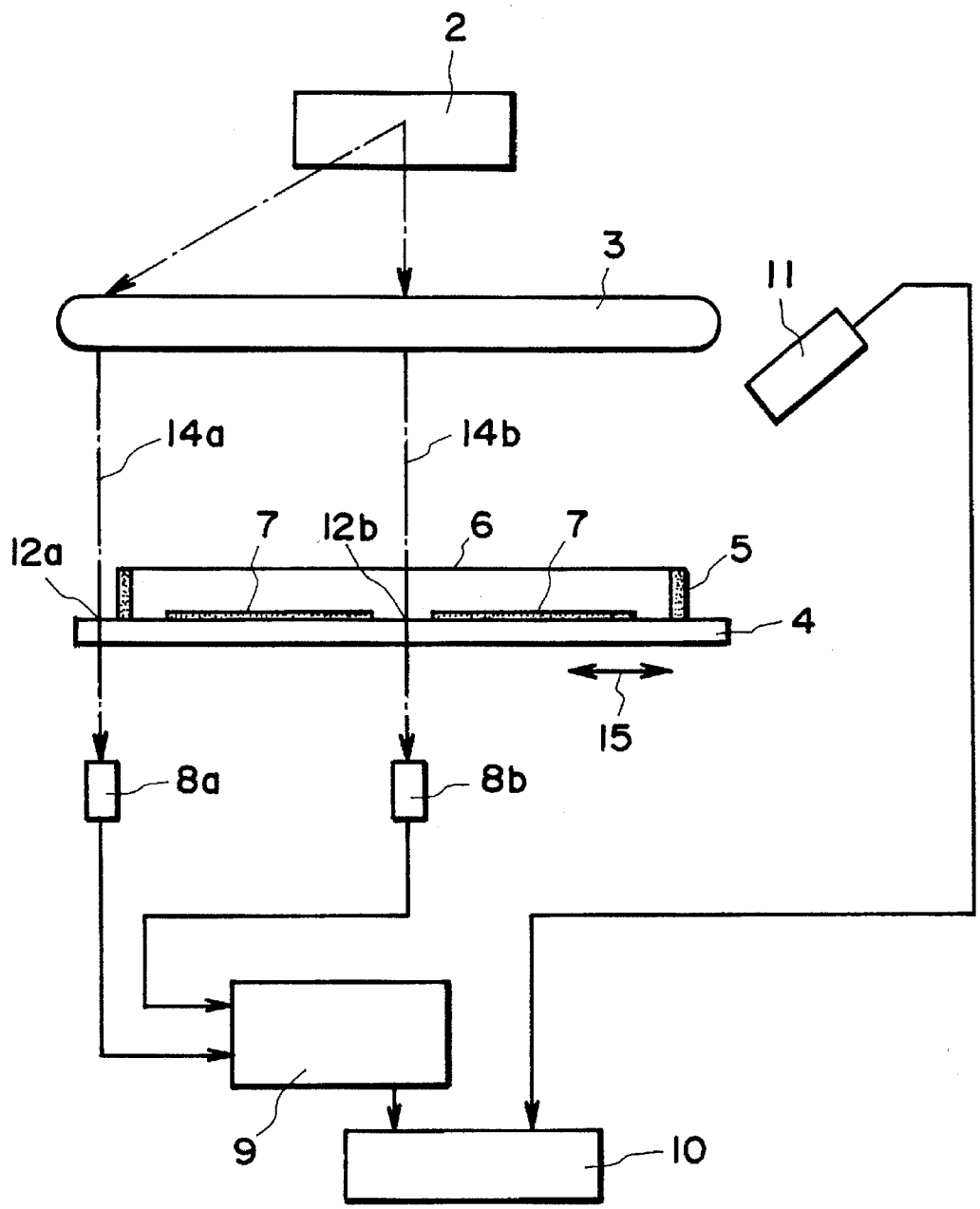
FIG. 2 is a side view of the main portion of the particle inspection system of the FIG. 1 embodiment.
Figure 3A:
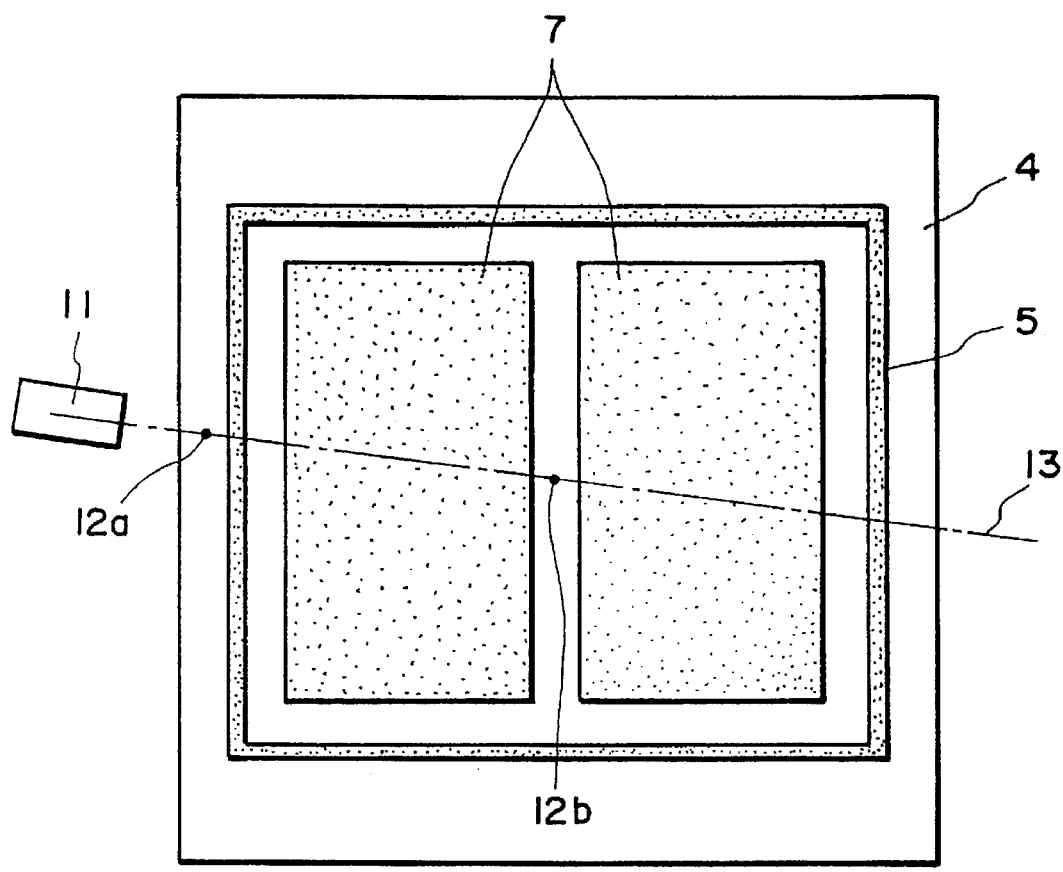
FIGS. 3A and 3B are enlarged views of a portion of FIG. 1.
Figure 3B:
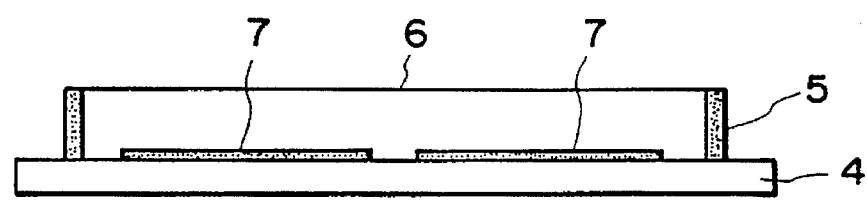

FIG. 1 is a sectional view of a first embodiment of the present invention. FIG. 2 is a side view of the embodiment of FIG. 1, and FIGS. 3A and 3B are enlarged views for explaining a portion of FIG. 1.

Denoted in FIG. 1 at 1 is a light source which comprises an Ar laser, for example. Denoted at 2 is a scanning system for reflectively deflecting light 14 from the light source 1.

In this embodiment, the scanning system 2 has a galvano mirror. However, it may use a polygonal mirror, for example. Denoted at 2a is an actuator for driving the scanning system 2. Denoted at 3 is an f-θ lens for directing the light, deflected by the scanning system 2, to the surface to be inspected (surface with a pattern) of an original 4 for inspection. Denoted at 7 is a circuit pattern formed on the surface of the original 4.

In FIG. 1, the original 4 surface is scanned with light from the scanning system 2 and the f-θ lens 3, in a direction perpendicular to the sheet of the drawing of FIG. 1 (a direction along the sheet of the drawing of FIG. 1).

Denoted at 6 is a pellicle (protection film), which serves to protect the original 4 with a pellicle supporting frame 5 so as to prevent adhesion of particles onto the circuit pattern 7 of the original 4. Denoted at 8 (8a or 8b) is photoelectric converter means. The photoelectric converter means detects the light intensity as the light 14 (14a or 14b) is at the position 12 (12a or 12b). Denoted at 9 is a first signal processing system for comparing outputs of the photoelectric detectors 8a and 8b to calculate the transmissivity of the pellicle 6 in accordance with a formula to be described later.

Denoted at 11 is a photoelectric converter for detecting scattered light from a particle which lies on the surface of the original 4 being inspected. Denoted at 10 is a second signal processing system. When a particle is present, from an output of the photoelectric converter 11 and a signal from the processing system 9, the second signal processing system 10 serves to correct the intensity of scattered light from that particle and to calculate the particle diameter or position thereof, for example.

In FIGS. 3A and 3B, depicted at 13 is the locus of irradiation as defined by the light 14 scanning the original 4. This will be called a "scan line", hereinafter. The scan line 13 is inclined by about 15 deg. with respect to a side of the original 4. This is to avoid scattered light from the circuit pattern 7, since major pattern lines of the circuit pattern 7 extend with angles 0 deg., 45 deg. and 90 deg. with respect to the side of the original 4. The point 12a on the original 4 corresponds to the position on the original 4, in a region outside the pellicle frame 5. There is no chromium deposition in this region, and therefore, the region is transmissive. The point 12b corresponds to the position inside the pellicle supporting frame 5, in a region in which there is no circuit pattern 7 on the original and in which there is no chromium deposition. Thus, this region is transmissive.

The operation of the inspection system of this embodiment will be described below. The light 14 from the light source 1 is reflectively deflected by the scanning system 2, and it passes the pupil of the f-θ lens 3. The light is transformed by this f-θ lens 3 into light advancing approximately parallel to the optical axis of the f-θ lens, and it scans the original 4 surface along the scan line 13 shown in FIG. 3A. If a particle is present on the scan line, the light 14 is scattered by the particle. The thus produced scattered light is detected by the photodetector 11 and it is photoelectrically converted. Simultaneously, the original 4 is moved in the direction as depicted by an arrow 15 in FIG. 1, such that the whole surface of the original 4 is scanned two-dimensionally.

In this embodiment, the proportional relationship between the particle diameter of a particle and the light intensity of the scattered light from that particle is detected beforehand and corresponding data is memorized in the signal processing system 10 beforehand. Thus, by detecting the magnitude of the light intensity of scattered light from a particle, the size or magnitude of the particle is discriminated in the signal processing system 10. If the particle size is large enough to damage the pattern transfer precision, the original is not fed into in the exposure process but is fed into a re-cleaning process, as will be described later.

It is possible that pellicles 6 of different manufacture lots have different thicknesses. The actual light intensity of the light 14 changes with a change in the thickness of the pellicle.

In this embodiment, in consideration of this, the transmissivity of a pellicle 6 is measured by using the light 14 and the photoelectric converting means 8 (8a or 8b). Based on the measured transmissivity, correction is made to the light intensity of the scattered light. The pellicle transmissivity measurement is performed as follows.

The light intensity P1 of light passing a first predetermined position and the light intensity P2 of light passing a second predetermined position are compared with each other. More specifically, in FIGS. 2 and 3A, (i) the light intensity P1 of light 14a passing a predetermined position 12a which is on the scan line 13 and which is in a transparent region of the original 4 outside the pellicle supporting frame 5 and (ii) the light intensity P2 of light 14b passing through the pellicle film 6 and through another predetermined position 12b which is in another transparent region of the original 4, are compared with each other. Based on this comparison, the transmissivity TP of this pellicle 6 is determined in accordance with equation (1) below:

$$TP = P2/P1 \quad (1)$$

In this embodiment, the transmissivity of the pellicle 6 is calculated by the processing system 9 in accordance with equation (1), and the resultant value is applied to the signal processing system 10. Then, the detected value of the photoelectric converting means 11 is divided by the calculated pellicle transmissivity by which any effect due to a change in the scattered light resulting from a change in the pellicle transmissivity is removed. Thus, accurate discrimination of particle diameter is assured.

[Embodiment 2]

Figure 4:
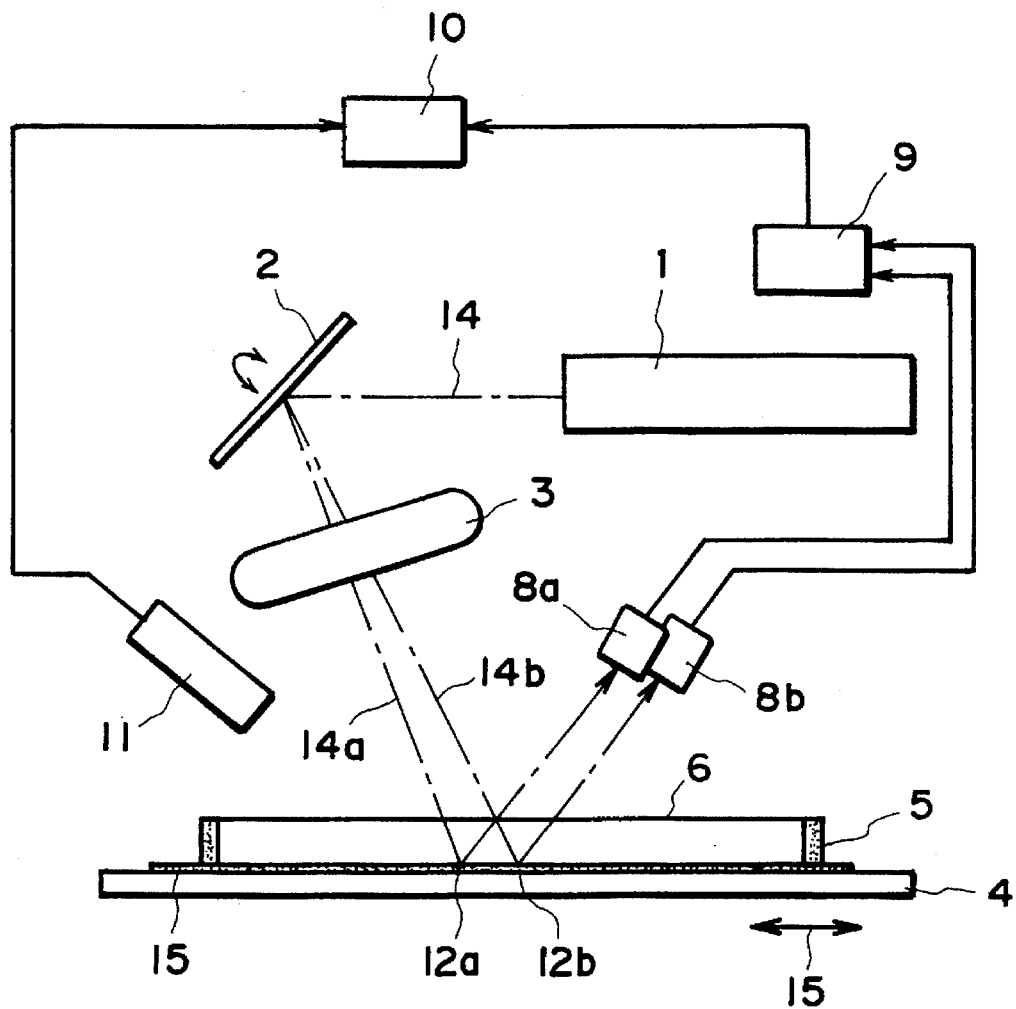
FIG. 4 is a schematic sectional view of a main portion of a particle inspection system according to a second embodiment of the present invention.
Figure 5:
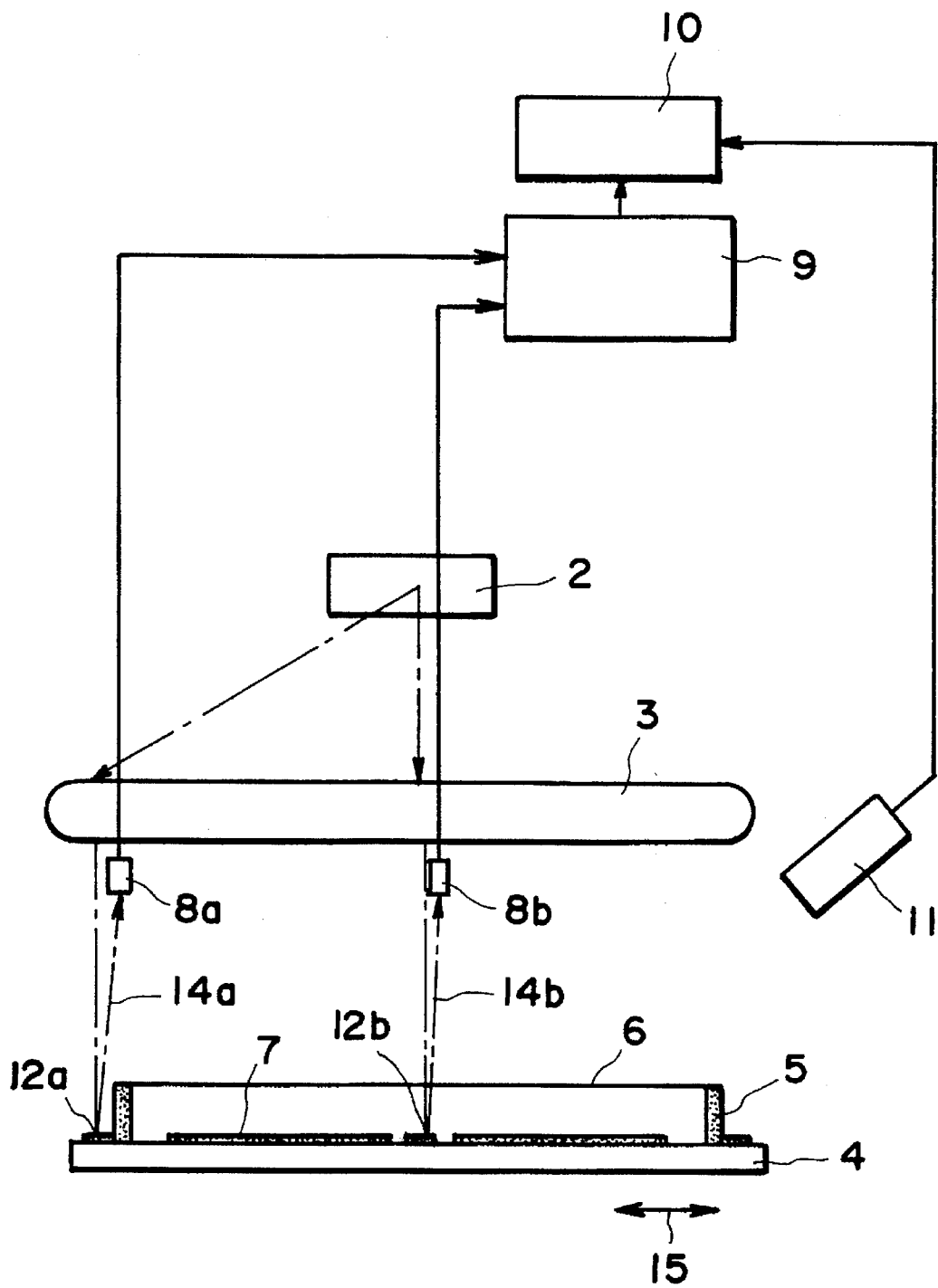
FIG. 5 is a side view of the main portion of the particle inspection system of the FIG. 4 embodiment.

FIG. 4 is a schematic sectional view of a main portion of an inspection system according to a second embodiment of the present invention. FIG. 5 is a side view of the inspection system of FIG. 4, and FIGS. 6A and 6B and 7A and 7B each is an enlarged view of a portion of FIG. 4.

In the first embodiment of FIG. 1, the pellicle transmissivity is measured by using light intensities of the lights passing the positions 12a and 12b on the original 4. On the other hand, the present embodiment comprises a reflection type wherein reflector means 15 is provided at the positions corresponding to the points 12a and 12b on the original, such that the pellicle transmissivity is determined by using reflected light. The remaining portion of this embodiment has substantially the same structure as that of the first embodiment.

Figure 6A:
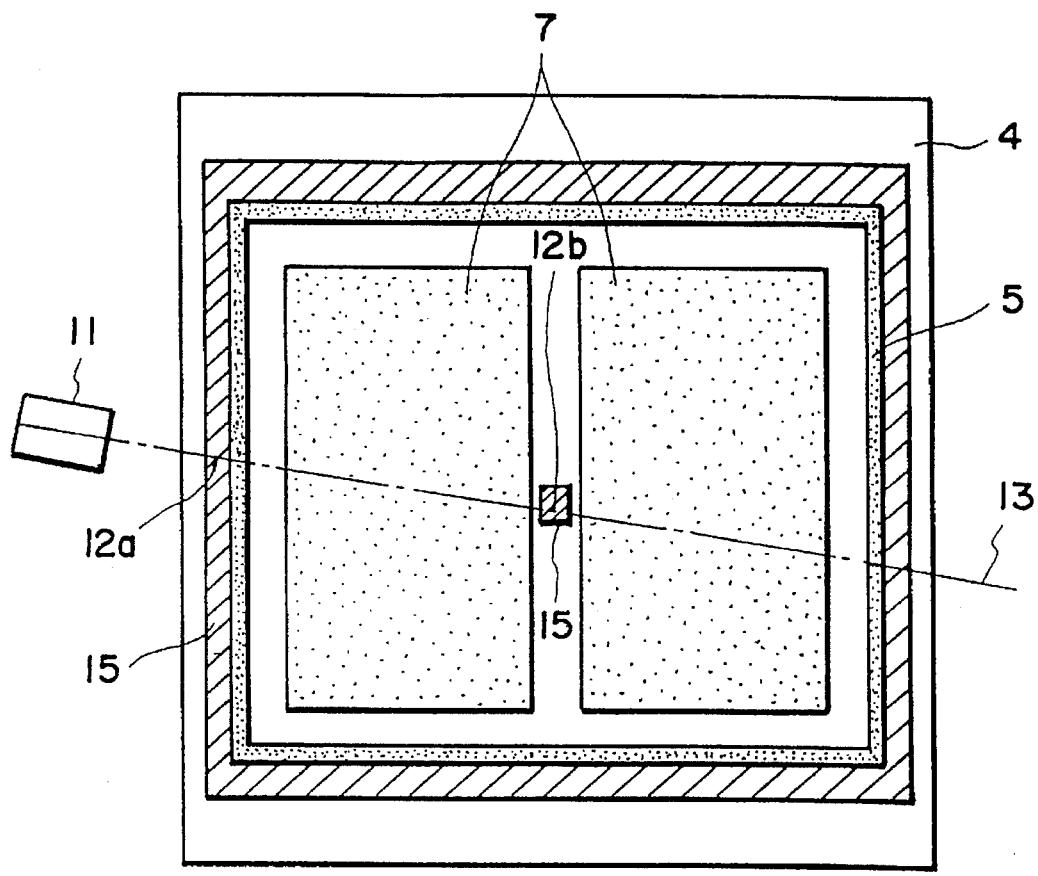
FIGS. 6A and 6B are enlarged views of a portion of FIG. 4.
Figure 6B:
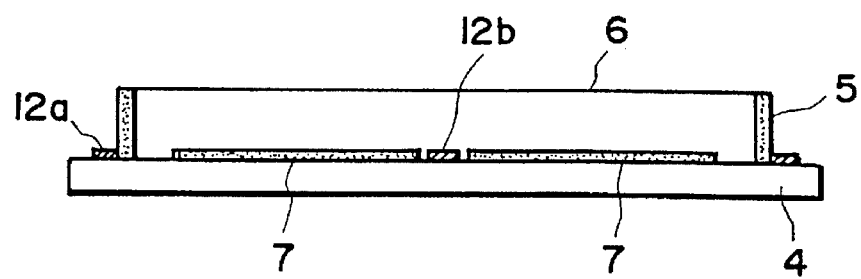

In FIGS. 6A and 6B, denoted at 12a is a predetermined position on the Original 4 which is outside the pellicle supporting frame 5. The position 12a is within a region coated by deposition with a reflective material 15 such as chromium, for example. Denoted at 12b is another predetermined position on the original 4 which is inside the pellicle supporting frame 5. The position 12b is within a region coated by deposition with a reflective material such as chromium, for example.

In FIG. 6, comparison is made between (i) the light intensity P1 of light 14a reflected at a predetermined position 12a which is a reflective portion of the original 4 placed on the scan line 13 and outside the pellicle supporting frame 5 and (ii) the light intensity P2 of light 14b passing the pellicle 6 and another predetermined position 12b which is a reflective portion of the original 4, and the transmissivity of the pellicle 6 is calculated in accordance with the following equation:

$$TP = \sqrt{(P2/P1)} \quad (2)$$

The signal processing system 9 calculates the transmissivity TP of the pellicle 6 by using equation (2), and it applies the resultant value to the processing system 10. In this manner, any effect due to a change in scattered light caused by a change in the pellicle transmissivity is avoided, and accurate discrimination of particle diameter is assured.

Figure 7A:
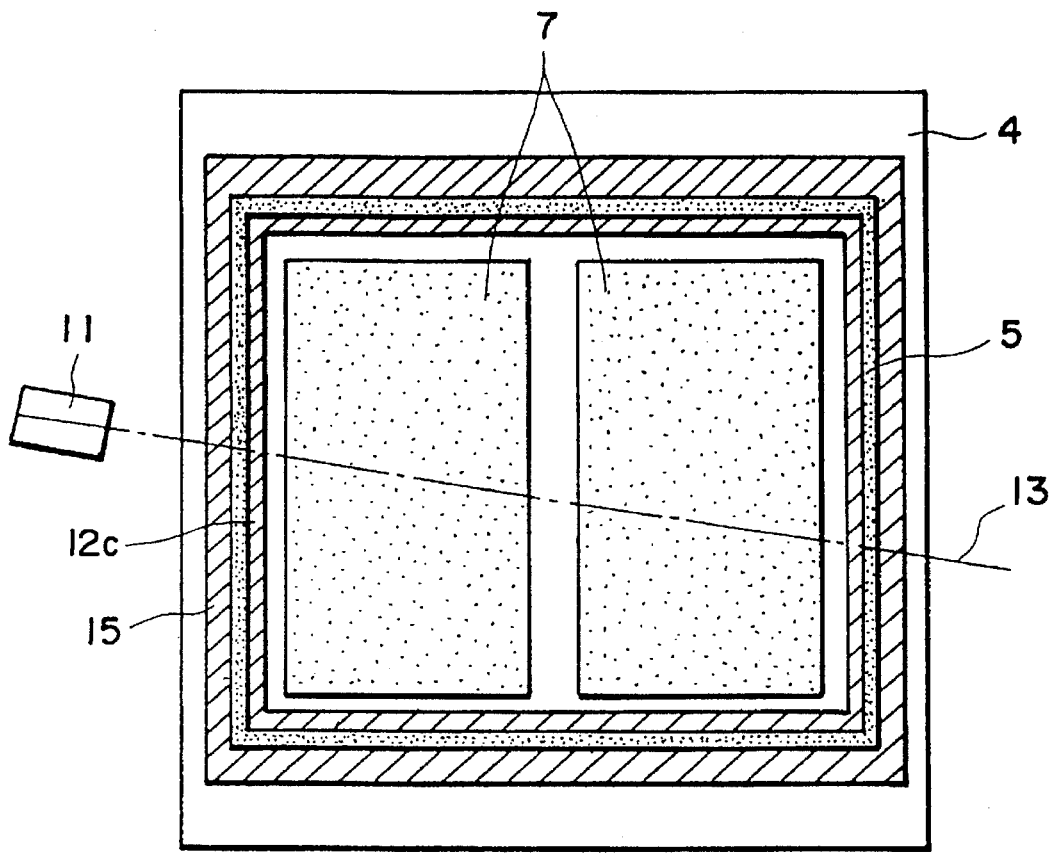
FIGS. 7A and 7B are enlarged view of a portion of FIG. 4.
Figure 7B:
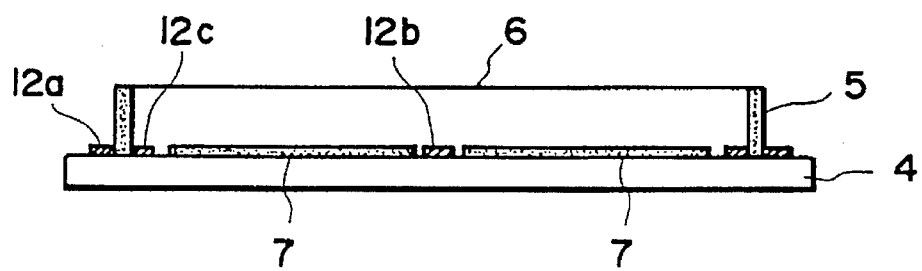

If, in this embodiment, it is not possible to provide a reflective portion close to the center of the original 4, a reflective portion may be defined at a predetermined position 12c shown in FIGS. 7A and 7B which is inside and close to the pellicle supporting frame 5, such that reflected light from the position 12c may be detected by a photodetector 8b disposed opposed to the position 12c.

[Embodiment 3]

Figure 8:
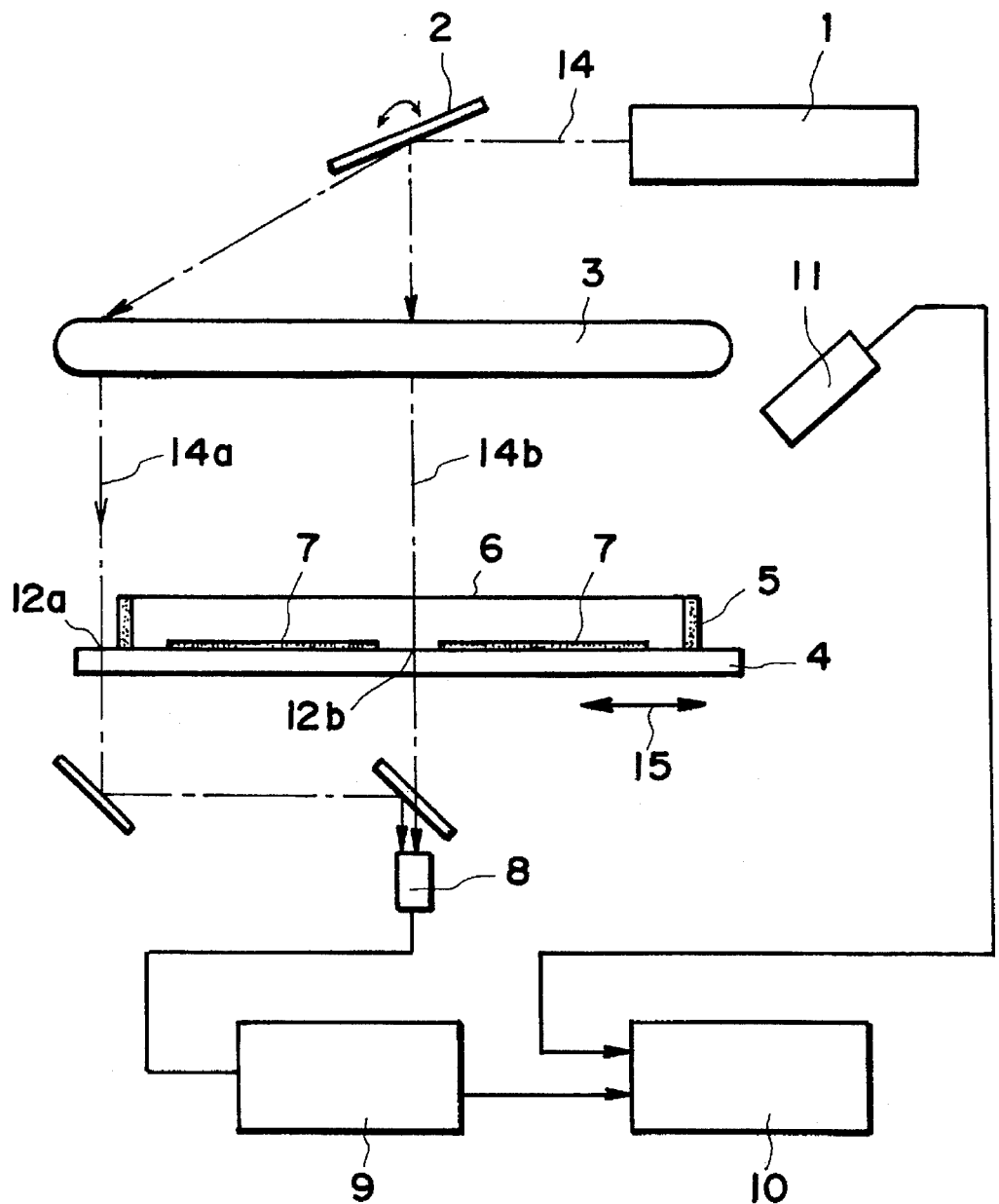
FIG. 8 is a schematic view of a main portion of a particle inspection system according to a third embodiment of the present invention.

FIG. 8 is a schematic sectional view of an inspection system according to a third embodiment of the present invention.

As compared with the first embodiment of FIG. 1, this embodiment has a feature that lights 14a and 14b passing predetermined points 12a and 12b on the original 4 are detected by using one and the same photoelectric converter 8. The remaining portion of this embodiment has substantially the same structure as that of the first embodiment.

With the arrangement of this embodiment, there is no possibility of detection sensitivity variation between separate photoelectric converters, and the particle diameter discrimination is performed with higher accuracy.

[Embodiment 4]

Figure 9:
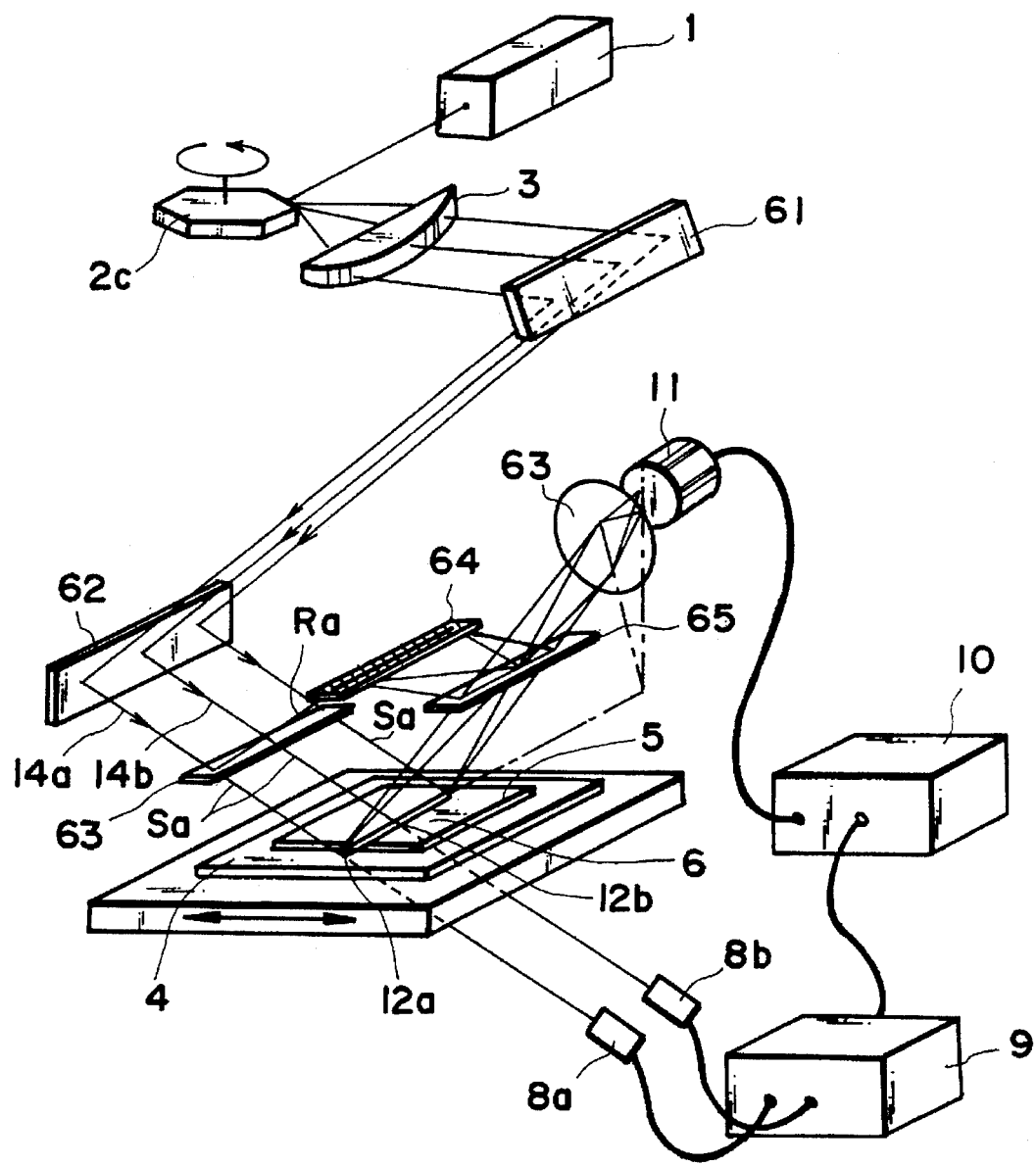
FIG. 9 is a schematic view of a main portion of a particle inspection system according to a fourth embodiment of the present invention.

FIG. 9 is a schematic view of an inspection system according to a fourth embodiment of the present invention.

As compared with the first embodiment of FIG. 1, this embodiment has a feature that a heterodyne interference optical system capable of detecting the presence/absence of a more minute particle is adopted and the transmissivity of a pellicle is measured.

It is to be noted that the concept of this embodiment may be applied to a reflection type system such as illustrated in FIG. 5.

In FIG. 9, like numerals as those of FIG. 1 are assigned to corresponding elements. Denoted in FIG. 9 at 1 is a light source which comprises a dual-frequency laser. Denoted at 61 and 62 are mirrors each for changing the scanning light path. Denoted at 63 is a polarization beam splitter which serves to split the light from the dual-frequency laser 1 with respect to the polarization plane, by which reference light Ra and illumination light Sa to be directed to the original 4 are produced. Denoted at 64 is a diffraction grating for diffracting the reference light Ra sidewardly. Denoted at 65 is a half mirror for combining the reference light Ra and scattered light Sb. The manner of measuring the transmissivity of the pellicle 6 is the same as that in the first embodiment of FIG. 1.

Now, how to detect a particle by using the heterodyne method in this embodiment, will be described.

The laser beam from the dual-frequency laser light source 1 is directed to a scanning optical system which comprises a scanning mirror 2c and an f-θ lens 3, whereby the light is scanningly deflected. Then, the light goes via the mirrors 61 and 62 and, thereafter, the light is split by the polarization beam splitter 63 into an S-polarized illumination laser beam Sa (shift frequency w) and a P-polarized reference laser beam Ra (shift frequency w+Δw). The split S-polarized laser beam Sa impinges on the surface 4 to be inspected. Scattered light produced by a particle or a fault or, alternatively, by a circuit pattern 7, being present in the range of the light projected, is received by a condensing lens 63 which is disposed aside in the direction of about 90 deg. to the incidence direction of the S-polarized laser beam Sa. In response, the condensing lens provides sidewardly scattered light SSa which passes the half mirror 65 and is collected.

On the other hand, diffraction light is produced in response to impingement of the P-polarized laser beam Ra upon the diffraction grating 64. Of the thus produced diffraction light, first-order diffraction light Ra1 is diffracted toward the half mirror 65. The half mirror 65 combines the first order diffraction light Ra1 and the sideward scattered light SSa. The diffraction grating 64 is arranged so that first order diffraction light is produced in a sideward direction approximately at 90 deg. to the incidence direction of input light and it is assuredly combined with the sideward scattered light SSa by the half mirror 65 in accordance with the position of light being moved by the scanning optical system.

A P-polarized component contained in the sideward scattered light as combined by the half mirror 65 (as resulting from depolarization by the particle or fault) and the first order diffraction light (P-polarized component) from the diffraction grating 64, are imaged by the condensing optical system 63 upon the sensor surface of the photoelectric detecting means 11, whereby optical heterodyne interference is produced. A signal based on this interference is processed by a beat signal processing system 10.

In this embodiment, as described, the heterodyne method is used and, additionally, the transmissivity of the pellicle 6 is used as a correction value to perform high precision detection of particle information about the presence/absence of a particle and/or the diameter size thereof.

[Embodiment 5]

Figure 10:
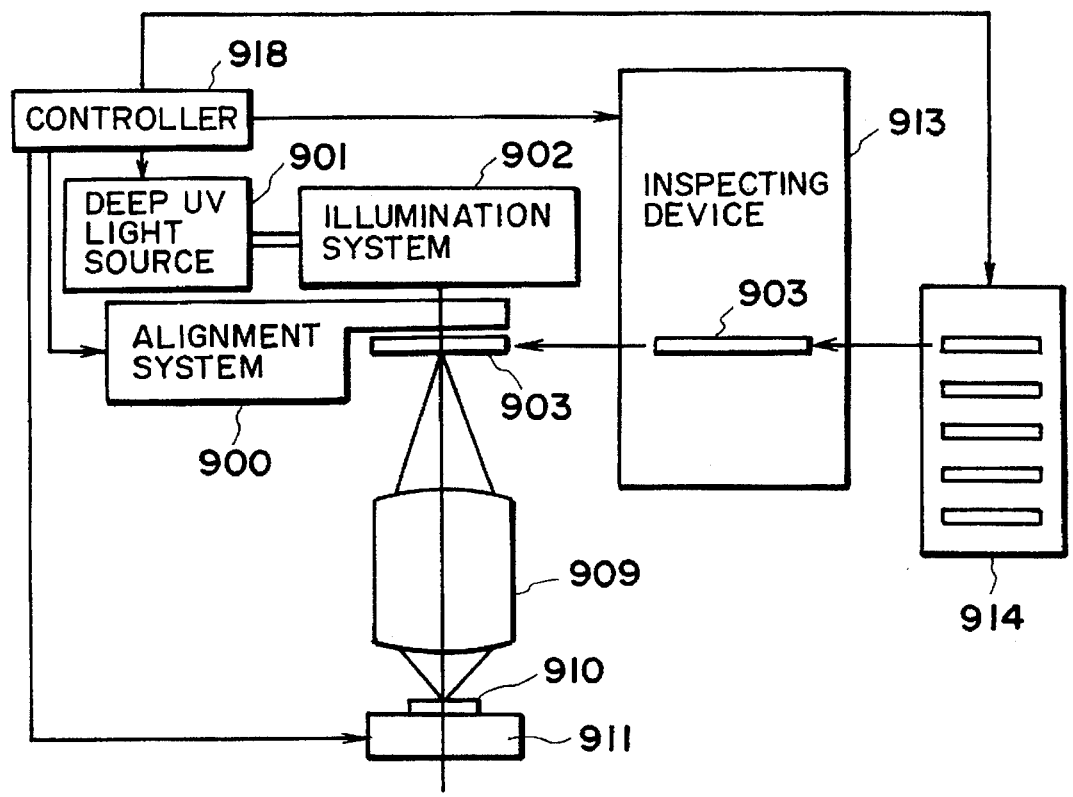
FIG. 10 is a schematic view of a main portion of a particle inspection system according to a fifth embodiment of the present invention.

FIG. 10 is a schematic view of an inspection system according to a fifth embodiment of the present invention.

In this embodiment, the invention is applied to a manufacturing system for manufacturing semiconductor devices by printing a circuit pattern of an original, such as a reticle or photomask, on a wafer. The manufacturing system generally comprises an exposure apparatus, an original accommodating device, an original inspecting system and a controller, all being housed in a clean room.

Denoted in FIG. 10 at 901 is a deep ultraviolet light source such as an excimer laser. Denoted at 902 is an illumination system of unit structure, which cooperates with the light source 901 to illuminate the whole surface of an original 903, placed at the exposure station EP, from above and with a predetermined numerical aperture (N.A.). Denoted at 909 is a projection lens for projecting and printing a circuit pattern, formed on the original 903, on a wafer 910 such as a silicon substrate, for example. For the projection exposure (printing), the exposure process is repeated while shifting the wafer 901 shot by shot, in accordance with stepwise motion of a movable stage 911. Denoted at 900 is an alignment system which serves to align the original 903 and the wafer 910 with each other, prior to the exposure operation. The alignment system 900 comprises at least one original observation microscope system. The elements described above are components of the exposure apparatus.

Denoted at 914 is an accommodating device for originals, and it accommodates a plurality of originals therein. Denoted at 913 is an inspection system (particle inspection system) for inspecting the presence/absence of a particle on an original. This inspection system has the same structure as that of any one of the embodiments described hereinbefore. The inspection system 913 serves to perform particle inspection to an original selected, after the same is taken out of the accommodating device 9 and before the same is set at the exposure station EP.

The principle and process of this particle inspection are based on any one of the embodiments described hereinbefore. Controller 918 serves to perform sequence control to the manufacturing system as a whole, and specifically it controls the operations of the accommodating device 914 and the inspection system 913 as well as the sequences of basic operations of the exposure apparatus, such as alignment operation, exposure operation, wafer stepwise feeding operation and the like.

Next, the semiconductor device manufacturing processes using the manufacturing system of this embodiment will be explained.

First, an original 903 to be used is taken out of the accommodating device 914, and it is placed in the inspection system 913.

Subsequently, in this inspection system 913, particle inspection is performed to the original 903. If absence of a particle is discriminated as a result of inspection, the original is then placed at the exposure station EP.

Then, a semiconductor wafer 910 to be exposed is placed on the movable stage 911. After this, the pattern of the original is projected in reduced scale on each zone of the semiconductor wafer 910 while moving the same stepwise (shot by shot) in accordance with the stepwise motion of the movable stage 911, through the step-and-repeat method.

When exposure of the whole wafer 910 surface is completed, the wafer is unloaded and accommodated in a container, and a subsequent wafer is supplied. Then, a similar step-and-repeat exposure process is performed to execute the pattern printing operation again.

Exposed wafers, having been processed by the exposure process, are then treated in a known manner by a developing process, an etching process and the like with appropriate structures provided separately from the manufacturing system. Then, an assembling process such as a dicing operation, a wire bonding operation, or a packaging operation is performed whereby semiconductor devices are manufactured.

[Embodiment 6]

Figure 11:
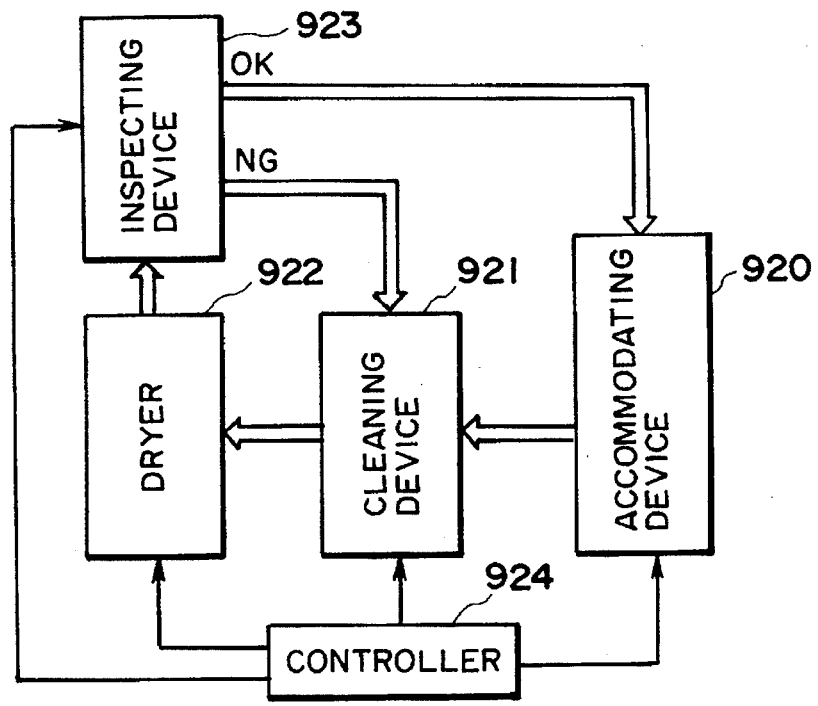
FIG. 11 is a block diagram of a main portion of a cleaning and inspection system according to the present invention.
Figure 12:
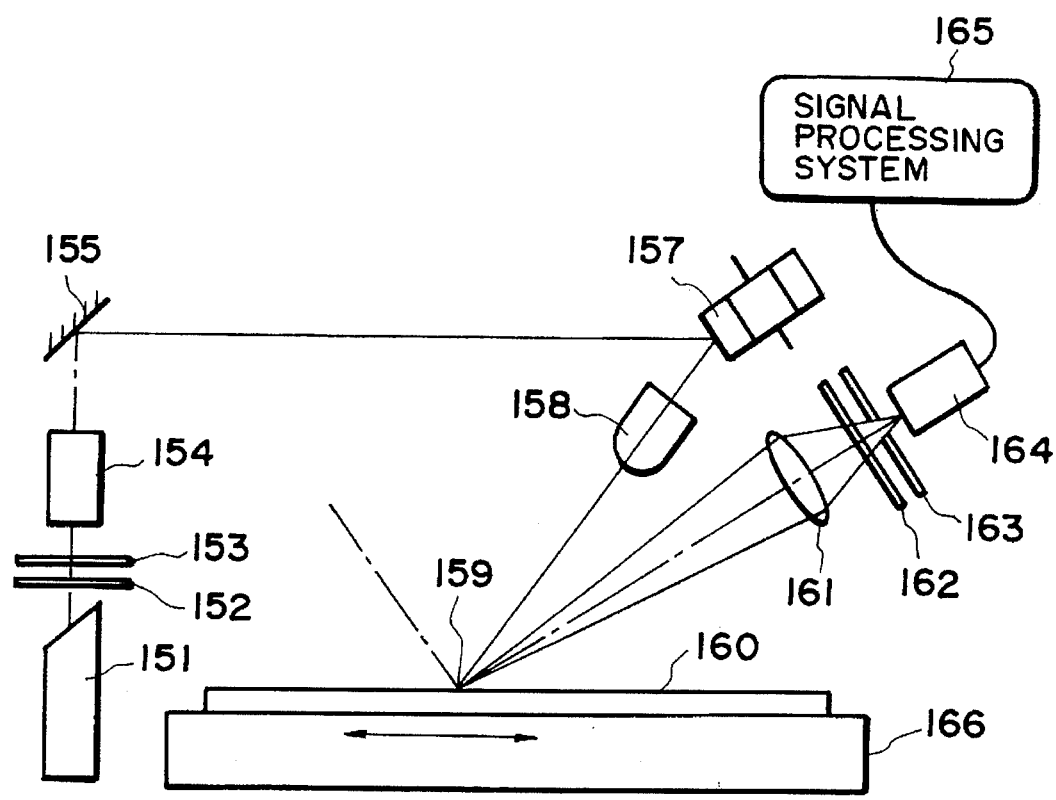
FIG. 12 is a schematic view of a known type particle inspection system.
Figure 13:
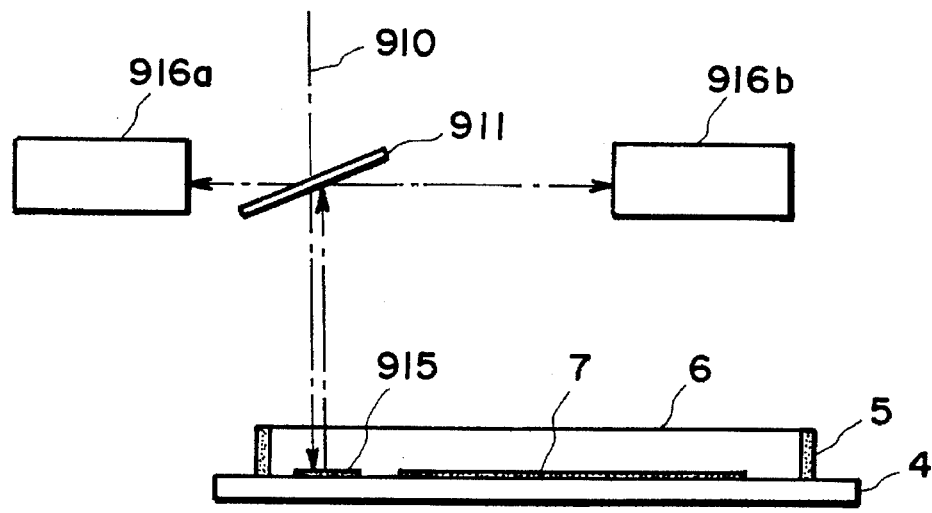
FIG. 13 is a schematic view for explaining a known type pellicle transmissivity measuring system.

FIG. 11 is a block diagram of an original cleaning and inspection system for the manufacture of semiconductor devices, according to an embodiment of the present invention. The cleaning and inspecting system generally comprises an original accommodating device, a cleaning device, a drying device, an inspecting device and a controller, all being housed in a clean room.

Denoted in FIG. 11 at 920 is an original accommodating device for accommodating a plurality of originals therein. An original to be cleaned is supplied from this accommodating device. Denoted at 921 is a cleaning device for washing an original by using pure water. Denoted at 922 is a drying device for drying a cleaned original. Denoted at 923 is an original inspecting device having the structure the same as that of any one of the embodiments described hereinbefore. It serves to perform particle inspection to a cleaned original. Denoted at 924 is a controller which serves to perform sequence control to the cleaning and inspecting system as a whole.

In operation, first an original to be cleaned is taken out of the original accommodating device 920. It is then fed into to the cleaning device 921. After the original is cleaned by the cleaning device 921, it is fed into the drying device 922, whereby it is dried. After the drying process is completed, the original is moved into the inspecting device 923, in which the particle inspection to this original is performed in accordance with any one of the methods of the preceding embodiments.

If no particle is detected in the inspection, the original is moved back into the accommodating device 920. If a particle is detected, the original is moved back into the cleaning device 921, and the cleaning process is performed again. After drying it in the dryer device 922, inspection of it is performed again through the inspecting device 923. This procedure is repeated until all particles are removed from the original. A satisfactorily cleaned original is moved back into the accommodating device 920.

Subsequently, a cleaned original is placed in the exposure apparatus, and the circuit pattern of that original is printed on a semiconductor wafer, and semiconductor devices are manufactured.

While the invention has been described with reference to the structures disclosed herein, it is not confined to the details set forth and this application is intended to cover such modifications or changes as may come within the purposes of the improvements or the scope of the following claims.

What is claimed is:

1. An inspection system for inspecting an original with a pellicle, said system comprising:

a light source for providing a light beam;

first detecting means for receiving light produced as a result of passage of the light beam through the pellicle, said first detecting means receiving light via both the pellicle and the original;

second detecting means for receiving light produced as a result of non-passage of the light beam through the pellicle, said second detecting means receiving light via the original but not via the pellicle; and determining means for determining information related to transmissivity of the pellicle, on the basis of outputs of said first and second detecting means.

2. A system according to claim 1, further comprising inspecting means for projecting the light beam from said light source to the surface of the original and for receiving scattered light produced thereby, to perform inspection of the original.

3. A system according to claim 2, further comprising correcting means for correcting a result of the inspection of the original on the basis of the information related to the transmissivity of the pellicle.

4. A system according to claim 1, wherein said first and second detecting means comprise a common detector.

5. An exposure system, comprising:

an inspection system as recited in any one of claims 1 and 3 through 5; and an exposure apparatus for transferring by exposure a pattern of an original having been inspected by said inspection system.

6. A cleaning and inspecting system, comprising:

an inspection system as recited in any one of claims 1 and 3 through 5; and a cleaning system for cleaning an original having been inspected by said inspection system.

* * * * *

UNITED STATES PATENT AND TRADEMARK OFFICE
CERTIFICATE OF CORRECTION

PATENT NO. : 5,652,657
DATED : July 29, 1997
INVENTOR(S) : MINORU YOSHII, ET AL.

It is certified that error appears in the above-identified patent and that said Letters Patent is hereby corrected as shown below:

ON THE COVER PAGE:

Under "ABSTRACT" item [57]

"system" should read --system for--.

COLUMN 1:

Line 16, "integrated (IC)" should read --integrated circuit (IC)--; and
Line 18, "photomask," should read --photomask--.

COLUMN 3:

Line 25, "40 deg." should read --40 deg.).--.

COLUMN 4:

Line 13, "view" should read --views--.

UNITED STATES PATENT AND TRADEMARK OFFICE
CERTIFICATE OF CORRECTION

| | | |
|---|---|---|
| PATENT NO. : | 5,652,657 | Page 2 of 2 |
| DATED : | July 29, 1997 | |
| INVENTOR(S) : | MINORU YOSHII, ET AL. | |

It is certified that error appears in the above-identified patent and that said Letters Patent is hereby corrected as shown below:

COLUMN 5:

Line 45, "into in the" should read --into the--.

COLUMN 6:

Line 1, "4," should read --4--;
     Line 30, "Original" should read --original--; and
     Line 39, "FIG. 6," should read --FIGS. 6A and 6B,--.

COLUMN 7:

Line 35, "particle" should read --particle,--.

Signed and Sealed this

Seventh Day of April, 1998

Attest:

BRUCE LEHMAN

*Attesting Officer*    Commissioner of Patents and Trademarks